United States Patent [19]
Cox et al.

[11] Patent Number: 5,283,072
[45] Date of Patent: Feb. 1, 1994

[54] MODIFIED AND SIMULATED LIQUID POULTRY EGG PRODUCTS AND METHODS OF MAKING THE SAME

[76] Inventors: James P. Cox; Jeanne M. Cox, both of 246 E. Bartlett Rd., Lynden, Wash. 98264

[21] Appl. No.: 674,495

[22] Filed: Mar. 25, 1991

Related U.S. Application Data

[63] Continuation-in-part of Ser. No. 349,974, May 8, 1989, which is a continuation of Ser. No. 196,878, May 19, 1988, abandoned, which is a continuation of Ser. No. 70,597, Jul. 8, 1987, abandoned, which is a continuation of Ser. No. 748,086, Jun. 24, 1985, abandoned.

[51] Int. Cl.⁵ .............................. A23B 5/10; A23B 5/16
[52] U.S. Cl. ..................... 426/312; 426/298; 426/299; 426/300; 426/313; 426/330.1
[58] Field of Search ............... 426/298, 299, 300, 312, 426/313, 330.1

[56] References Cited

U.S. PATENT DOCUMENTS

| | | | |
|---|---|---|---|
| 2,236,773 | 4/1941 | Fischer | 426/312 |
| 2,776,214 | 1/1957 | Lloyd et al. | 426/330.1 |
| 3,028,245 | 4/1962 | Mink et al. | 426/330.1 |
| 3,144,342 | 8/1964 | Collier et al. | 426/312 |
| 3,364,037 | 1/1968 | Mink | 426/330.1 |
| 3,658,558 | 4/1972 | Rogers et al. | 426/330.1 |
| 4,524,082 | 6/1985 | Loit | 426/330.1 |
| 4,524,083 | 6/1985 | Loit | 426/298 |

*Primary Examiner*—Jeannette Hunter
*Assistant Examiner*—Mary S. Mims
*Attorney, Agent, or Firm*—Hughes & Multer

[57] ABSTRACT

A blended yolk composition is disclosed comprised of a fat, an emulsifier and an aqueous component, at least one of the fat and the aqueous component containing a chicken-type flavoring. The yolk composition can be used in baking or combined with egg white, a modified egg white or a simulated egg white to produce a simulated blended whole poultry egg composition.

Alternatively the yolk composition may utilize a modified yolk, such as decholesterolized yolk. Also disclosed are methods of preparing the compositions.

13 Claims, No Drawings

MODIFIED AND SIMULATED LIQUID POULTRY EGG PRODUCTS AND METHODS OF MAKING THE SAME

CROSS REFERENCE TO RELATED APPLICATIONS

This application is a continuation-in-part of U.S. application No. 349, 974, filed May 8, 1989, copending herewith, which was a continuation of U.S. application No. 196,878, filed on May 19, 1988, and abandoned, which was a continuation of U.S. application No. 070,597, filed on Jul. 8, 1987, and abandoned, which was a continuation of U.S. application No. 748,086, filed on Jun. 24, 1985, and abandoned.

BACKGROUND OF THE INVENTION

Liquid egg substitute products have recently demonstrated increasing consumer acceptance. The primary benefit of these products is reduced fat, cholesterol and calories. Typical modified liquid poultry egg and simulated egg products suffer a variety of deficiencies when compared to natural poultry egg preparations particularly in organoleptic qualities, i.e., taste, aroma, mouth feel, texture and flavor. In particular, such products tend to be somewhat thick and grainy, and, when cooked, tend to be somewhat soft, fluffy or otherwise physically abnormal. Moreover, such products are typically deficient in functional parity compared to scrambled eggs and products made from poultry eggs.

In addition to the foregoing, microbiological stability before and during storage has been and continues to be a problem for liquid, modified, simulated and poultry egg compositions and products. A significant consideration of such products is that liquid poultry eggs and consequently products made therefrom contain differing degrees of microbial contaminants (such as salmonella) which can cause spoilage and illness. There are additional risks of cross-contamination upon mixing, processing and handling. Pasteurization processes retard bacterial spoilage for up to about 72 hours. Most liquid egg and egg products require frozen storage and defrosting prior to use. Despite freezing, some bacterial problems have persisted in those products.

Frozen egg replacement products are difficult for consumers to locate in stores and require thawing prior to use. In addition, if improperly stored, these products have a relatively high risk of bacterial spoilage.

Whether prepared for consumer or institutional use, various egg products have been pasteurized and dried. The drying usually is accomplished by spray drying, although in some instances the egg material is dried in a thin layer in a pan. The dried material may be ground to a powder of uniform consistency.

Poultry egg yolk is of greater commercial value than poultry egg white because the yolk contains the greatest nutrient value. It behaves as an emulsifier and may be used with or without egg white in various prepared foods such as pastries, cake mixes, souffles, sauces and pasta products. The modified and simulated liquid poultry egg compositions of the present invention are organoleptically, textually and functionally very similar to liquid poultry egg compositions and products made therefrom. Products of this invention are improved in keeping quality over ordinary liquid poultry egg compositions and do not necessarily contain cholesterol. They may also be reduced in fat and/or calories over ordinary poultry eggs.

This invention relates to simulated and liquid poultry egg products, products which ordinarily contain natural poultry eggs and products which ordinarily utilize yolks or blended whole poultry eggs such as scrambled eggs, egg patties, tube eggs, french toast batter, mayonnaise, souffles, omelets, hollandaise sauce, pancakes, waffles, pastries, egg nog and such.

As used herein, the term "modified" refers to compositions which contain components of natural egg in relatively large amounts, which have been treated to reduce the levels of fat and/or cholesterol contained therein, reduce or increase the viscosity of the product, or otherwise treated to affect the organoleptic or functional quality.

The term "simulated" refers to those products which do not contain a substantial quantity of a natural egg component in the composition.

For example, a yolk composition which contains a high concentration of decholesterolized natural yolk is referred to as a modified composition, whereas a yolk composition containing essentially no natural yolk is referred to as a simulated yolk composition.

The composition described herein can be used in place of natural poultry yolk, such as in baking, as well as in a blended composition containing the yolk composition and additional ingredients which when blended together with the yolk composition, simulate scrambled egg or a batter which is used as described above to simulate blended whole eggs.

Products produced in accordance with this invention may include poultry egg white, yolk or combinations thereof, as well as defatted, decholesterolized or otherwise modified natural egg components.

During processing, free glucose may be removed from the egg material by the action of bacteria, yeast or enzymes. Also, it may be desirable to stabilize the egg material or otherwise alter its physical properties. The resulting egg material may be stable in its dry form or may be preserved by refrigeration or freezing.

Compositions produced in accordance with the present invention resolve these organoleptic and functional problems, and are microbiologically more stable. After packaging, the compositions produced according to the invention may be frozen or simply refrigerated. When carefully processed and packaged, products can be made to provide extended keeping even when stored at room temperature.

One problem which has vexed egg substitutes prior to this invention is texture. They tend to have an unnatural fluffy, spongy or grainy consistency as described above.

When prepared using a microwave oven poultry and simulated poultry eggs become degraded organoleptically and cook unevenly. If slightly undercooked, there may be free running raw product mixed with cooked portions which may be somewhat rubbery. If overcooked, there may be a mixture of rubbery and even burnt portions in an abnormal chewy mass.

Products prepared from the present invention, whether provided in raw or pre-cooked form, substantially overcome these problems. Entrees may be made utilizing the composition of the invention which may be freeze thaw cycled numerous times.

When liquid egg products are processed in accordance with the present invention, they may be kept over extended periods of time without producing "off" flavors.

One object of the present invention is to provide modified and simulated poultry egg compositions which have substantially the same consistency as ordinary poultry yolk and blended poultry egg compositions, while imparting the same consistency as liquid poultry eggs to preparations and products made therefrom.

An additional object is to provide egg compositions which can be used as substitutes for blended whole poultry eggs or poultry egg yolks, exhibiting the characteristic effects of poultry eggs in preparations and products made therefrom.

It is a further object of the invention to provide a modified or simulated poultry egg composition which does not substantially separate on standing and is easily re-homogenized.

Another object of the invention is to provide a composition which can be employed in place of poultry egg yolk, and can be combined with egg whites or an equivalent thereto to closely simulate blended whole eggs or yolks in commercial food preparations.

An additional object is to provide a liquid modified, simulated poultry egg composition which is functionally equivalent to natural poultry egg and/or egg yolk, imparting the same or similar benefits to preparations when used as an ingredient.

Another object of the invention is to provide a simulated poultry egg yolk composition which contains essentially no poultry egg material.

It is also an object of the invention to provide a process for making simulated poultry egg compositions which are economical to use.

It is another object of the present invention to provide liquid modified and simulated poultry egg compositions as well as products containing such compositions which may be readily microwaved without noticeable substantial diminution in quality.

Another object of the invention is to provide liquid modified and simulated poultry egg compositions and products which are freeze/thaw stable whether raw or pre-cooked.

Another object of the invention is to provide a method and the product produced therefrom, which are safe to prepare and eat after packaging and storage for extended periods of time.

The foregoing objects can be accomplished by producing liquid, modified and simulated poultry egg and/or yolk compositions and products made therefrom that can be used as poultry yolk and blended whole egg substitutes to provide simulated and modified scrambled eggs, poached eggs, tube eggs, yolk for use in baking, pasta, pastry, omelets, french toast batter, pancakes, waffles, egg nog, mayonnaise, sauces, souffles and the like.

SUMMARY OF THE INVENTION

Modified and simulated poultry yolk and blended whole egg compositions and products which contain such compositions are described herein comprised of mixtures of a chicken flavored aqueous liquid, fat and algin, having substantially the same consistency as natural products.

Modified and simulated liquid poultry egg compositions and products produced therefrom are also described herein, comprised of a blend of the yolk composition and natural, modified or simulated poultry egg white, said blend having the approximate functional and organoleptic properties of liquid poultry eggs.

DETAILED DESCRIPTION

The composition of the invention can be substituted for liquid whole poultry egg or egg yolk in cooking, in the industrial preparation of foods such as for cake mixes, pastas, waffles, pancakes and french toast batter, and can be frozen raw in microwaveable containers, breakfast entrees, pastries, sauces such as Hollandaise sauce, mayonnaise, salad dressing and such.

The major ingredients contained in the composition are an aqueous poultry-flavored liquid or a substitute, such as dehydrated chicken broth and a vegetable, animal or poultry fat.

The most preferred aqueous poultry flavored liquid is natural poultry egg white, which can be included in the composition as described below. The aqueous liquid is preferably chicken broth (dried or aqueous) to provide a poultry flavor to the composition. When dried chicken broth is used as a flavorant, a quantity of water may also be added to assist in maintaining the proper consistency. A preferred substitute for chicken broth is hydrolyzed vegetable protein having a chicken-like flavor.

As used herein, the term "fat" includes both edible fats and oils. This component can be any edible, substantially non-cholesterol containing fat or oil, which is blendable with the aqueous ingredients and flavorant, and which will form a suitably stable emulsion with the aqueous material. Hence, an edible oil such as canola oil is preferred.

The fat (or oil) component can include poultry flavoring for the composition. For example, chicken fat or a flavored fat such as butter can be used, preferably in minor amounts, to avoid any substantial addition of cholesterol to the composition.

The components described above are blended with sufficient gums, colorants, stabilizers, preservatives and the like to render the blended composition substantially identical to natural poultry egg yolk in taste, aroma, texture, stability, cooking or baking properties and the like.

The fat component and aqueous component are typically emulsified through the use of the gums and/or stabilizers which are used in emulsifying amounts. As such, the gums can act as emulsifiers in and of themselves, or additional emulsifiers can be included.

To prepare a composition which simulates blended whole egg, the yolk composition described above is combined with natural egg white, treated egg white or a synthetic egg white in proportions which are equivalent to the proportion found in natural eggs, about 1 part yolk to about 1-5 parts of white.

One preferred gum which assists in imparting the desired consistency to the simulated egg yolk composition, and which substantially stabilizes the emulsified product is algin. The algin used can be of the low or high viscosity type. It is preferred that a combination of low and high viscosity algin be used.

If low viscosity algin alone is used, there should be a larger percentage concentration of algin than if high viscosity algin or a combination of low and high viscosity algin is used. It is more economical to include at least some high viscosity algin. Alternatively, the algin component can also include some medium viscosity algin. The amount of algin used in the composition should be such that the composition will have approximately the same consistency as natural egg yolk and the blend will stabilize.

Sufficient yellow food coloring can also be used to match the color of natural egg yolk.

One procedure for making the simulated poultry egg yolk composition is to blend the aqueous liquid, fat and the algin in a high-speed blender without the application of heat for a period of 15 to 20 minutes until the mass has attained homogeneity. The resulting semiliquid composition can be either frozen, dehydrated and powdered, or incorporated directly in cooked foods.

The composition can be mixed with powdered or liquid egg white and cooked to make a blend for preparing simulated scrambled eggs. It is preferred that the simulated egg yolk material be combined with natural egg white material in the proportion of 65 to 95 percent by weight egg white (preferably 77 percent) and 5 to 35 percent by weight yolk material (preferably 23 percent).

Alternatively, the simulated poultry egg yolk composition can be used in place of natural egg yolk in conventional recipes such as for making noodles or other pasta products or for making mayonnaise or salad dressing.

In making batter for french toast, natural egg white material and the simulated egg yolk material described above can be combined and then blended with milk (about 5-15% by weight).

An alternative process of the present invention includes deaeration of the composition at a vacuum pressure of between 20 to 30 in. Hg. until essentially all of the gas is disentrained from the liquid product. This is usually accomplished while the liquid batter is warmed, preferably below about 140° F. which is the coagulation point of the natural egg white constituents which are frequently used in the composition.

After deaerating the composition, precautions can be taken in subsequent processing steps to insure that ambient air is not re-incorporated at any point. Gasification with inert gas or combinations thereof, can be accomplished by entraining desired gases in the blend through gas lines, thereby supplying the deaerated product with inert gas upon restoration of atmospheric equilibrium. Inert gases are particularly useful for reducing the tendency of the product to spoil or support microbial growth.

The inert gases used may be selected from those commonly used in food products. For example, nitrogen or combinations of nitrogen and carbon dioxide may be used, and a preferred gas mixture is one containing nitrogen 75% and carbon dioxide 25%.

The egg substitute product can be made thin running and of very homogeneous consistency. It tends not to separate upon storage. Most importantly, when the product is poured onto a preheated cooking surface slowly and then folded over as the surface cooks, the final product is dense and nonporous, offering a firm texture which many consumers prefer.

If a fluffier product is desired, the liquid egg composition may simply be whipped with a fork or other mixing device, such as a whip or egg beater, to incorporate air, and a small quantity of milk can be added as would be done with natural poultry eggs. Thus, the product can be prepared in a wide variety of ways.

Additionally, the liquid egg product can be formulated to prepare crispy surfaces on baked products by adding some sugar or other glaze-producing ingredient to the blend. Some consumers desire this characteristic in french toast.

Additionally, when produced as described, the product does not require freezing for distribution even though it is substantially freeze-thaw stable. The prepared (cooked) product is also freeze-thaw stable and does not become watery, crumbly or rubbery when thawed and re-heated, such as by microwaving. In this respect, the product of the present invention is superior to natural poultry eggs.

The composition described herein may be cooked by any conventional method including microwaving. To microwave, the composition may be placed in a heatable container, such as a styrofoam cup, even in frozen form, and then placed in a microwave oven for a short cooking time e.g., 1 to about 3 minutes. To further facilitate preparation, a quantity of the composition equivalent to about two poultry eggs by weight (100 gms.) may be pre-poured into an 8 oz. disposable container and frozen solid. The cup is then simply removed and placed in a conventional household microwave oven (e.g., 700 watts) and microwaved. The cooked product may then be removed and eaten. The product resembles natural scrambled eggs which have been prepared on a stove top in a skillet.

Consequently, a wide variety of tasty, convenient products may be prepared as microwaveable breakfast entrees in this fashion, including scrambled eggs, egg sandwiches, french toast and the like.

Hollandaise sauce can be made from the simulated egg yolk material with or without milk, cream or sour cream, by including a small amount of lemon juice, salt and seasoning, such as a little hot pepper sauce or cayenne pepper.

Simulated whole eggs can be made by surrounding an amount of the simulated egg yolk material approximately equal to the amount of egg yolk in a natural egg with an amount of egg white approximately equal to that present in a natural egg and freezing the simulated egg yolk and egg white combination in an egg-shaped mold to produce a simulated natural poultry egg. To such quantity of simulated yolk material, a heat-activated coagulant is added selected from the group consisting of carbohydrate, protein and metal ionic material such as calcium which will set to a greater or lesser extent when heated. After being frozen, the simulated egg can be dipped into a liquid preparation forming calcium carbonate which will harden to form an egg shell if desired.

As described above, the vacuum deaeration step can be particularly useful for achieving the notable improvements in the products of this invention. Preferred processes are described in detail below.

Natural poultry egg white is charged into a refrigerated tank which is kept near freezing temperatures. The egg white is then pre-blended with any dry ingredients utilized at a reduced temperature, e.g., about 34° F., with continuous, slow agitation. The agitation may be continued for several minutes up to about an hour, at which time the blend may be treated with an enzyme deactivator, e.g, hydrogen peroxide, over a time period and at a temperature which are effective for substantially deactivating any pre-existing viable egg white enzymes, e.g., catalase, thus reducing any untoward reactions between the egg white and the other ingredients. Hydrogen peroxide is preferred, since it forms oxygen and water upon reaction. However, substantially pure oxygen gas can be used which is derived from other sources, e.g., bottled gas, UV or cathode generated oxygen gas and the like. The oxygen gas should be incorporated into the egg white before or during heating, and intimately mixed into the egg white blend, such as with a turbine, to cause intimate mixing with all parts of the blend.

The hydrogen peroxide is typically added to the egg white as about a 35% (w/v) solution and a suitable quantity of the peroxide solution is typically added which is equivalent to about 0.3% of the total weight of the final product. Due to the rapid generation of oxygen gas, the egg white may foam upon reaction with the peroxide. Hyperoxygenation of the liquid egg white portion of the formula occurs, and this has surprisingly been found to reduce the need for detergents, gums and emulsifiers which are useful for stabilizing the final product in emulsified form. Alternatively, emulsifiers such as Tween 60 can be used.

After processing and during the cooling step, the fats and oils may begin to solidify. The product may form a floc and begin to separate. The container should be agitated at this point before additional chilling to preclude further separation without any substantial diminution in quality. Hence the final emulsified product is relatively stable upon standing. The resulting product is more free-flowing and has a smooth consistency.

The flavor of the egg white pre-blend is relatively unaltered by this step, since the oils and colorants need not be present during this peroxide treatment. Consequently, oxidation of the oils which would lead to rancidity and oxidative changes of the colorants can be avoided, and there need not be any alteration of the flavor/aroma profile as would be expected with whole egg. Additionally, nitrogen gas may be added to the blend of egg white ingredients to aid in removing any ing any oxygen gas saturated in the blend.

The oil and colorant components are typically pre-blended together and heat treated prior to combining them with the egg white after the egg white and peroxide have reacted completely, as judged by the cessation of bubbles, or after the dissolved oxygen gas is otherwise removed.

The oil and colorant components are combined in a container and heated to about 180° to 300° F. for a time period effective for rendering the mixture substantially free of microorganisms, e.g., from about 10 minutes to about 10 hours.

After mixing the egg white and dried ingredients and chilling this mixture, the chilled egg white/dried ingredient blend is rapidly heated to a temperature of about 115° F. to about 120° F. The preferred method of rapidly heating the egg white/dried ingredient blend is through the use of a heat exchanger, which utilizes a hot water flow at a temperature of about 165° to 170° F. After this initial heating step, the peroxide solution is added as described above. At temperatures in this range, the peroxide is added slowly to avoid overfoaming, prolong the release of oxygen and avoid over-treatment of the egg white. If oxygen gas is aggressively added, the temperature may be raised through the heat exchanger more rapidly to a higher temperature, e.g., about 125° to about 139° F.

After this rapid heating step, the egg white blend is heated to a higher temperature, just below the protein coagulation temperature. This further reduces the activity of any enzymes present, and heat pasteurizes the egg white blend. This temperature typically ranges from about 135° F. to about 148° F. over a few minutes. At about 120° F., enzyme activity of the blend decreases substantially and at about 125° F. the enzymes are denatured. It should be noted that pasteurization can be accomplished at higher temperatures, such as about 160° to about 180° F. if the heating time is reduced sufficiently to avoid unwanted coagulation.

The heating step described above should be continued until the peroxide has reacted completely, so that essentially no hydrogen peroxide remains in the egg white blend. The presence of hydrogen peroxide, as well as the presence of peroxidase and catalase, may detract from the stability of the composition, and can be detected using the tests described below.

Alternatively, if oxygen is added from a source other than peroxide, the oxygen can be displaced with nitrogen gas prior to the addition of the oil components. Additionally, an oxygen scavenger such as glucose oxidase, can be utilized to assist in removing oxygen from the egg white blend prior to the addition of the oil components.

The oil/colorant blend is preheated and then combined with the essentially peroxide and oxygen-free egg white blend. This combination produces the final blended product, which is then typically subjected to vacuum and packaging steps.

After the oil/colorant blend is added to the egg white blend, the temperature can be maintained at the pasteurization temperature for about 10 minutes to 90 minutes, preferably about 15 minutes.

Upon completion of the heating cycle, the formulation is passed while hot into a vacuum chamber, where about a 25 to 30 in. Hg. vacuum is applied to the formulation. By creating negative pressure within the chamber, the formulation may be drawn into the chamber. The formulation may be continuously agitated while under negative pressure through the use of a static mixing tube which homogenizes the formulation. The formulation may be recirculated under vacuum, such as with a recirculating pump located in the vacuum loop. By drawing the formulation off at the bottom of the vacuum tank and recirculating it back through the static mixing tube under vacuum, the formulation may be homogenized and the level of dissolved gas in the formulation substantially reduced.

The vacuum chamber may optionally be allowed to pressure equilibrate with an inert gas, e.g., nitrogen or carbon dioxide gas. This optional step allows the dissolved gas level in the product to increase and equilibrate without allowing ambient air to contact the product. The vacuum tank pressure is then reduced as previously described. Glucose oxidase may then be added when the temperature of the blend is about 135° F. or below.

When the level of oxygen gas has been sufficiently reduced in the formulation, and with the blend at a temperature of about 110° F. to about 120° F., the formulation may be cooled rapidly to about 50° F. or lower. This cool-down step may utilize a heat exchanger as previously described, using a cold water flow instead of hot water as described above.

The formulation may then be transferred into a chill tank where it is gently agitated and further cooled to a temperature slightly above freezing, e.g., 33° F.

The product may then be aseptically fed into a filling-/capping device, and packaged under positive filtered air pressure.

The heat treatment of the chilled formulation at the beginning of the process and the rapid chill down at the end of the process facilitate and enhance stabilization of the emulsified end product, and reduce the potential for bacterial contamination. Temperature changes in the pre-blended components and in the chill down at the end of the process can be made rapidly to minimize the time at which the blends are at "incubation temperatures," thus minimizing bacterial colonization. Anaerobic microorganisms are typically destroyed by the peroxide reaction or oxygen treatment, and aeromicroorganisms are destroyed by the pasteurization process. Any remaining aerobic bacteria are rendered substantially inactive in the oxygen deficient/inert gas environment, which is largely non-supportive of bacterial growth.

The resultant product is quite stable even after 16 to 18 weeks at variable temperatures, e.g., about 36° F. to 44° F., when kept in an aseptically sealed container. Culture tests of samples have demonstrated bacterial levels of 0 to <10 microorganisms per gram.

Since enzyme concentrations can be expected to vary somewhat from batch to batch in natural egg white, since the evolution and rate of evolution of oxygen gas from the peroxide reaction are important to stabilization, and since all hydrogen peroxide is desirably removed from the product, it is important to ascertain the peroxide and enzyme levels in the blend at various stages.

Tests have been developed for quick determinations of both peroxidase and catalase activity, and the presence of residual hydrogen peroxide.

To test for the presence of catalase or peroxidase:

In a 25 ml. test tube, combine 12.5 mls. of egg white and 12.5 mls. of distilled water at 75° F. Using a standard 7 mm. paper punch, punch a disc from Whatman #1 filter paper. Using forceps, dip the disc into a 3% solution of hydrogenperoxide. Shake excess peroxide from disc, and insert the disc into the test tube beneath the surface of the diluted egg white. Release the disc and time the disc as it falls in the tube. It should freely fall down the tube toward the bottom. As the absorbed peroxide reacts with the enzyme, free oxygen forms on the surface of the disc, and it achieves neutral and then positive buoyancy in a direct relationship to the amount of oxygen generated. Stop the watch when the disc has returned to the surface of the tube.

The measurement of time is directly proportional to the level of enzyme activity and is a quick test for enzyme presence and activity. Standard times range from 3 to 15 seconds. For every ten second interval beyond 15 seconds, the peroxide treatment period is lengthened by about 5 minutes.

To test for residual peroxidase activity in the product:

Instill 25 mls. of 6% hydrogen peroxide into a test tube. Dip the disc into the processed egg white formulation, soaking through. Shake off the excess, and drop into the test tube. The disc should descend to the bottom and should not rise back to the top for at least 3 minutes. If enzymes are present, the disc will rapidly rise to the surface.

When oxygen gas is utilized in the blend as described above, an oxygen redox potential meter can alternatively be used to determine the level of free oxygen remaining in the blend.

EXAMPLE 1

A representative formula for the preferred simulated poultry egg yolk composition is as follows:

| Ingredient | Weight |
| --- | --- |
| Chicken broth | 74.850% |
| Chicken and/or poultry fat | 22.455% |

-continued

| Ingredient | Weight |
| --- | --- |
| Low viscosity algin powder | 2.246% |
| High viscosity algin powder | 0.449% |
| Total | 100.000% |

The proportion of the various ingredients can be varied as follows:

| Ingredient | Weight |
| --- | --- |
| Chicken-flavor aqueous liquid | 70.0 to 80.0% |
| Vegetable and/or poultry fat | 18.0 to 26.0% |
| Algin | 1.0 to 10.0% |
| Total | 100.0% |

EXAMPLE 2

| Yolk Composition | |
| --- | --- |
| Ingredient | Weight |
| Dried chicken broth | 15.52 gms. |
| Egg white | 2.28 lbs. |
| Canola oil | 0.14 lbs. |
| Sodium alginate | 7.04 gms. |
| Lecithin | 66.00 gms. |
| Butter culture | 5.80 gms. |
| Tween (polysorbate 60) | 1.97 gms. |
| Sodium stearoyl lactylate | 1.03 gms. |
| beta-carotene | 0.01 gms. |
| Yellow food dye | 0.60 gms. |
| Table salt | q.s. |

PROCEDURE

Combine egg white, sodium alginate, dried chicken broth, and salt in a main process tank. Agitate until the ingredients mix well, approximately 1 hour. Slowly feed the mixture through a heat exchanger (30+plate double pass) heated to 165° F. to 170° F. into a tank, raising the temperature of the blend to between 100° and 105° F. Maintain the blend in the enclosed heated agitation tank. Add 0.3% by weight of a 35% solution of hydrogen peroxide. Agitate with a small, internal turbine type mixer inserted into the tank. The mixing assists in contacting peroxide with the egg white enzymes and breaks up oxygen gas bubbles for rapid release.

Separately combine all other ingredients in a sealed container. Heat to about 250° F. for 25 minutes while keeping the container sealed until added to the egg white formula.

After the hydrogen peroxide has been added to the egg white blend and the foam has cleared, add 0.3 to 0.6% gaseous nitrogen through a turbine (2000 to 28000rpm) and with the temperature above 102° F., aseptically add the oil, dye, butter culture, lecithin, polysorbate 60, and sodium stearoyl lactylate, and continue to raise the temperature to between 138° and 139° F.

Continue agitation for at least 10 minutes at this temperature, then transfer into a vacuum tank.

Upon completion of this transfer, recirculate the product through the vacuum tank and a passive mixer at a vacuum pressure of 30 in. Hg.

When all bubbles have visibly been removed (as viewed through a vacuum tank porthole) and when the product tests negative for hydrogen peroxide or demonstrates less than 300 ppm dissolved oxygen as per an oxygen redox potential meter, transfer through a heat exchanger fed with water at 33° to 34° F. into a chill tank.

Feed the deaerated product from the chill tank into a filling and capping machine and package. After packaging, the product may be refrigerated or frozen for distribution.

After processing, samples were subjected to routine microbiological surveys. The average plate count was <10 colonies per cm$^2$.

Prior to processing blend samples yielded values ranging from 4,000 to 125,000 colonies per cm$^2$.

EXAMPLE 3

All ingredients from Example 2 are combined in a primary mixing tank while agitating. The temperature is rapidly raised to 137°-139° F. by circulating the blend through the heat exchanger. Oxygen gas is introduced through the agitator (approximately 0.2 to 0.5 lbs per 100 lbs of blend).

When the ingredients have become completely blended and homogenized, they are transferred to a vacuum/agitation tank which has been evacuated by vacuum pump at a negative pressure between 23 and 30 in. Hg. Evacuation of gas from the liquid egg product is completed within about 10 minutes while the blend is circulated and continuously agitated. Gaseous nitrogen may be added at this stage at a rate of about 0.2 to 0.6 lbs per 100 lbs of blend, and the blend may be re-evacuated as appropriate. The temperature is maintained within the range of 137° to 139° F. throughout the deaeration step.

When this deaeration step is complete (no more visible bubbles), the liquid egg product is transferred to a packing machine. Nitrogen gas may be flushed into the product and the product packaged. After packaging, store at 138° to 139° F. for 0.5-2 hours. The product should be intermittently agitated during the heated storage step.

Alternatively, the packages may be placed in a heated water bath and agitated by gently shaking for about the same period of time. The packaged product is rapidly cooled by placing in a pre-cooler or by contacting with sub-zero air or icy water while agitating. When the product has been cooled to about 45° F., it is transferred to refrigerator temperatures, e.g. 33° F., or frozen for distribution.

EXAMPLE 4

Following the same procedures as outlined in Example 2, liquid egg yolk which has been processed to remove cholesterol and reduce fat is combined with antioxidant effective amounts of alpha-tocopherol (about 1% by weight of the egg yolk). Sufficient beta-carotene is added to compensate for any loss of color due to reduction during the oxygenation step.

EXAMPLE 5

| BLENDED EGG COMPOSITION | |
|---|---|
| Ingredient | Weight |
| Decholesterolized Egg Yolk | 20 lbs. |
| Egg white | 162 lbs. |
| Dried chicken broth | 2 lbs. |
| Butter flavored corn oil | 6 lbs. |
| Sodium alginate (Kelco) | 1 lbs. |
| Beta-carotene | 0.005 lbs. |
| Hydrogen peroxide, 20% | 0.12 lbs. |

| -continued | |
|---|---|
| BLENDED EGG COMPOSITION | |
| Ingredient | Weight |
| Food grade silicone | 0.02 lbs. |
| Butylated hydroxyanisole (BHA) | 0.0001 lbs. |
| alpha-tocopherol | 0.05 lbs. |
| glucose oxidase | q.s. up to 10000 units per 100 lbs of formulation |
| TOTAL | 191.1451 lbs. |

We claim:

1. A process for improving the keeping quality of a simulated scrambled egg composition comprised of a blend of egg white and fat comprising:
   intimately treating the composition with an oxidizing gas in an amount effective for reducing the bacterial count;
   heating the composition to a temperature effective for further reducing the bacterial count without substantially denaturing the composition;
   degassing the composition, and
   cooling the composition at a rate sufficient to stabilize the blend.

2. A method of improving the keeping quality of a liquid egg product comprising:
   introducing an edible oxidizing gas into the liquid egg product under conditions which promote intimate contact with the liquid egg product and which reduce the bacterial count of the liquid product; and
   thereafter treating the liquid egg product while in a liquid state to remove substantially all of the edible oxidizing gas.

3. A method of improving the keeping quality of a liquid egg product comprised of introducing an edible oxidizing gas into the liquid egg product under conditions which promote intimate contact with the liquid egg product in a sufficient quantity, at a sufficient temperature and for a sufficient time to reduce the bacterial count;
   treating the liquid egg product to substantially remove the edible oxidizing gas, and
   introducing into the liquid egg product a nonoxidizing gas in a amount sufficient to promote retention of the keeping quality in the liquid egg product.

4. A process for producing a simulated scrambled egg composition with a shelf life extended over that of untreated simulated scrambled egg compositions, comprised of an emulsion of non-fat egg white and fat, comprising:
   intimately treating the non-fat portion with an edible oxidizing gas in an amount effective for reducing the bacterial count of the non-fat portion;
   heating the non-fat portion to a temperature effective for reducing the bacterial count without substantially denaturing the egg white;
   separately treating the fat portion by heating the fat to a temperature for a time period effective for reducing the bacterial count of the fat;
   treating the fat portion with a non-oxidizing gas;
   blending the fat and non-fat portions to form an emulsion;
   deaerating the emulsion, and
   cooling the emulsion at a rate sufficient to stabilize the composition.

5. In a process for producing a simulated scrambled poultry egg composition comprised of a blend of egg white, a fat and algin, the improvement comprised of so inhibiting enzyme induced oxidation of the composition by treating the egg white with oxygen as to deactivate enzymes present in the egg white and then blending the egg white with the fat.

6. The process described in claim 5 wherein the oxygen is generated from hydrogen peroxide.

7. The process of claim 5 wherein the oxygen is oxygen gas.

8. In a process for producing a simulated scrambled poultry egg composition wherein egg white, fat, algin and poultry flavorant are blended, an improvement comprised of reducing the tendency of the composition to spoil or support microbial growth by pasteurizing the composition and then placing the composition under vacuum at a pressure and under conditions effective for so deaerating the composition as to inactivate aerobic bacteria remaining in the composition after 9. A method of reducing the bacterial count of an egg white and fat containing composition comprising treating the egg white with hydrogen peroxide at a concentration, for a time and at a temperature effective for reducing the enzyme content of the egg white and then blending the egg white with the fat.

10. The method of claim 9 wherein the hydrogen peroxide is used in an amount which is equivalent to about 0.3% of the total weight of the egg white containing composition.

11. The method of claim 9 wherein the egg white is treated with hydrogen peroxide at an initial temperature of about 110° F. to 125° F., and the temperature is raised to about 130° F.

12. The method of claim 9 further comprising maintaining the egg white at an effective temperature for pasteurizing the egg white without substantially denaturing the egg white.

13. A process for stabilizing a simulated scrambled egg composition comprised of egg white, fat, poultry flavorant and algin comprising:

treating the egg white with oxygen in an amount effective for reducing the bacterial count of the egg white;

heating the egg white, poultry flavorant and oxygen to a temperature effective for substantially removing the oxygen without substantially denaturing the egg white;

heating the fat to a temperature for a time period effective for reducing the bacterial count of the fat;

blending the heated egg white, flavorant and fat to form a blend, and cooling the blend at a rate sufficient to stabilize the composition.

* * * * *